(12) United States Patent
Yeh et al.

(10) Patent No.: US 12,023,055 B2
(45) Date of Patent: Jul. 2, 2024

(54) BALLOON CATHETER SYSTEM ASSISTED BY ULTRASOUND AND MICROBUBBLES AND METHOD FOR VASODILATION

(71) Applicant: National Tsing Hua University, Hsinchu (TW)

(72) Inventors: Chih-Kuang Yeh, Hsinchu (TW); Chieh-Yu Tsai, Hsinchu (TW); Jen-Kuang Lee, Hsinchu (TW); Chun-Yen Lai, Hsinchu (TW); Zong-Han Hsieh, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 99 days.

(21) Appl. No.: 17/410,232

(22) Filed: Aug. 24, 2021

(65) Prior Publication Data
US 2022/0054155 A1    Feb. 24, 2022

Related U.S. Application Data

(60) Provisional application No. 63/069,190, filed on Aug. 24, 2020.

(51) Int. Cl.
*A61B 17/22* (2006.01)
*A61K 41/00* (2020.01)

(52) U.S. Cl.
CPC ...... *A61B 17/2202* (2013.01); *A61K 41/0028* (2013.01); *A61B 2017/22008* (2013.01);
(Continued)

(58) Field of Classification Search
CPC ........... A61B 2017/22001; A61B 2017/22002; A61B 17/22004; A61B 2017/22005;
(Continued)

(56) References Cited

U.S. PATENT DOCUMENTS 4,841,977 A * 6/1989 Griffith .................... A61B 8/12
  29/25.35
5,773,027 A * 6/1998 Bergeron ........... A61K 31/7068
  514/934
(Continued)

FOREIGN PATENT DOCUMENTS

CN    1519041 A    8/2004
CN    101405040 A    4/2009
(Continued)

OTHER PUBLICATIONS

China Patent Office "Search Report" issued on Nov. 24, 2021, China.

*Primary Examiner* — Shaun L David
*Assistant Examiner* — Mitchell Brian Hoag
(74) *Attorney, Agent, or Firm* — Juan Carlos A. Marquez; Marquez IP Law Office, PLLC

(57) ABSTRACT

A balloon catheter system assisted by ultrasound and microbubbles and a method for vasodilation are provided. The system includes: a controller; a sensor catheter; a highly focused ultrasound probe, and the highly focused ultrasound probe and the sensor catheter is connected to the controller; and a balloon catheter. The method of vasodilation includes: providing a sensor catheter into a blood vessel, and controlling a highly focused ultrasound probe to focus at a hardened portion of the blood vessel; removing the sensor catheter from the blood vessel and inserting a balloon catheter into the blood vessel; infusing microbubbles into the balloon catheter and controlling the highly focused ultrasound probe to start working to destroy a calcification point of the hardened portion of the blood vessel, and smoothly inflating the balloon catheter at the hardened portion of the blood vessel.

2 Claims, 14 Drawing Sheets

(52) U.S. Cl.
CPC ............... *A61B 2017/22062* (2013.01); *A61B 2017/22065* (2013.01); *A61B 2017/22082* (2013.01); *A61B 2017/22088* (2013.01); *A61B 2017/22089* (2013.01)

(58) Field of Classification Search
CPC ........... A61B 2017/22007; A61B 2017/22008; A61B 2017/22009; A61B 2017/22011; A61B 17/22012; A61B 2017/22014; A61B 2017/22017; A61B 2017/22018; A61B 17/2202; A61B 2017/22021; A61B 2017/22022; A61B 2017/22024; A61B 2017/22025; A61B 2017/22027; A61B 2017/22028; A61M 29/00; A61M 25/104; A61K 41/0028
USPC ......................................................... 606/128
See application file for complete search history.

(56) References Cited

U.S. PATENT DOCUMENTS

| | | | | |
|---|---|---|---|---|
| 6,004,269 | A * | 12/1999 | Crowley | A61B 8/445 600/374 |
| 2004/0019318 | A1 * | 1/2004 | Wilson | A61B 17/2202 604/22 |
| 2007/0010702 | A1 * | 1/2007 | Wang | A61L 31/10 424/422 |
| 2007/0041961 | A1 | 2/2007 | Hwang et al. | |
| 2009/0191244 | A1 * | 7/2009 | Kheir | A61P 7/00 514/789 |
| 2011/0196412 | A1 * | 8/2011 | Levit | A61M 25/10181 606/192 |
| 2011/0201974 | A1 * | 8/2011 | Soltani | A61B 17/2202 601/2 |
| 2012/0172720 | A1 * | 7/2012 | Asami | A61N 7/02 600/431 |
| 2013/0023802 | A1 * | 1/2013 | McIntosh | A61M 25/10 601/2 |
| 2013/0023897 | A1 * | 1/2013 | Wallace | A61B 17/22004 606/128 |
| 2014/0039358 | A1 * | 2/2014 | Zhou | A61M 37/0092 601/3 |
| 2014/0114216 | A1 * | 4/2014 | Konofagou | A61B 8/0808 601/2 |
| 2015/0374879 | A1 * | 12/2015 | DiMauro | A61M 25/1002 606/192 |
| 2018/0071505 | A1 * | 3/2018 | Lo | A61K 9/0009 |
| 2018/0132754 | A1 * | 5/2018 | Kusumoto | A61B 5/282 |
| 2018/0303503 | A1 * | 10/2018 | Eggert | A61M 25/1018 |
| 2019/0046667 | A1 * | 2/2019 | Wang | A61K 49/223 |
| 2019/0374763 | A1 * | 12/2019 | Lin | C07K 14/47 |
| 2020/0196596 | A1 * | 6/2020 | Menze | A01N 1/0289 |
| 2020/0338172 | A1 * | 10/2020 | Pacella | A61K 9/5015 |
| 2021/0015751 | A1 * | 1/2021 | Kim | B01F 23/808 |
| 2021/0275247 | A1 * | 9/2021 | Schultheis | A61B 18/1492 |
| 2022/0401574 | A1 * | 12/2022 | Villanueva | A61K 47/665 |

FOREIGN PATENT DOCUMENTS

| | | |
|---|---|---|
| CN | 101090670 B | 5/2010 |
| CN | 101883557 A | 11/2010 |
| CN | 102475682 B | 3/2013 |
| CN | 205548629 U | 9/2016 |
| CN | 107614052 A | 1/2018 |
| CN | 108883204 A | 11/2018 |
| CN | 110237256 A | 9/2019 |
| CN | 110381854 A | 10/2019 |
| CN | 110548140 A | 12/2019 |
| CN | 110811762 A | 2/2020 |
| CN | 111568500 A | 8/2020 |

* cited by examiner

BALLOON CATHETER SYSTEM ASSISTED BY ULTRASOUND AND MICROBUBBLES AND METHOD FOR VASODILATION

CROSS REFERENCE TO RELATED APPLICATION

The present application claims the benefit of the U.S. Provisional Application No. 63/069,190 filed on 24 Aug. 2020; the disclosure of which is incorporated herein by reference in its entirety.

BACKGROUND

Technical Field

The present invention relates to a balloon catheter device, and more particularly, this invention relates to a balloon catheter system assisted by ultrasound and microbubbles and a method for vasodilation.

Related Art

Atherosclerosis is a common chronic disease nowadays, which can compress blood vessels and lead to blockage of blood flow, and in severe cases, to stroke and other problems. Calcification is a type of atherosclerosis and is often considered a sign of the existence of atherosclerosis. When vascular calcification happens, the walls of blood vessels harden and lose their elasticity, making the contraction and diastole of blood vessels less functional. Moreover, when there is an excessive deposition of calcium on the walls of blood vessels, it can be considered vascular calcification. There are many treatment methods for atherosclerosis, such as laser ablation and rotational atherectomy. The most popular and affordable method is balloon angioplasty, which uses high water pressure to inflate a balloon catheter, resulting in revascularization of blood vessels. When the symptoms of atherosclerosis are too severe, however, the balloon often fails to inflate and eventually balloon rupture occurs, resulting in the risk in surgery.

Therefore, a method is proposed to greatly reduce the risk. By using the principle that ultrasound can oscillate microbubbles and generate cavitation, we integrate this technology into the balloon catheter to treat vascular sclerosis resulted from atherosclerosis. Experiments shows such method can effectively destroy the calcium structure and then help inflate the balloon catheters. The product is categorized into internal probe design and external probe design.

SUMMARY

The present invention is directed to solve the problem of failed balloon inflation in surgery; or the problem of surgical risk resulted from rupture of balloons, when calcification is too severe.

In one embodiment, the present invention provides a balloon catheter system assisted by ultrasound and microbubbles, including: a controller; a sensor catheter; a highly focused ultrasound probe, the highly focused ultrasound probe and the sensor catheter connected to the controller; and a balloon catheter.

In another embodiment, the present invention provides a method for vasodilation, including: providing a sensor catheter into a blood vessel, and controlling a highly focused ultrasound probe to focus at a hardened portion of the blood vessel; removing the sensor catheter from the blood vessel and inserting a balloon catheter into the blood vessel; infusing microbubbles into the balloon catheter and controlling the highly focused ultrasound probe to start working to destroy a calcification point of the hardened portion of the blood vessel; smoothly inflating the balloon catheter at the hardened portion of the blood vessel.

Young's modulus is also called elastic modulus. Pascal (Pa) is the unit of pressure in material mechanics and is often used at the scale of billion Pascal (GPa) in engineering. When an elastic material is subjected to a normal stress, a normal strain is generated. When the deformation does not exceed a certain elastic limit of the corresponding material, the ratio of the normal stress to the normal strain is obtained. Generally, the Young's modulus of in vivo calcification is about 20-40 GPa; for heavy calcification, the Young's modulus can reach 35-90 GPa or higher.

For simulating general calcification in vivo (Young's modulus of 20-40 GPa), 58.8% plaster is implemented as a vascular calcification model, with thickness of 3 mm and Young's modulus of 12.3 GPa. For heavy calcification (Young's modulus of 35-90 GPa or higher), 80.6% plaster as a model is implemented, with thickness of 3 mm and Young's modulus of 110-130 GPa. The purpose of the study is to assist inflation of balloon catheters in calcified blood vessels with ultrasound-induced microbubble oscillation, and therefore the Young's modulus of the calcification model is the most important consideration while producing the vascular calcification model.

In elasticity measurement, there are methods for measuring the Young's modulus. In the present invention, a non-destructive testing method with transverse wave probes is used to confirm whether the 58.8% plaster model has a similar Young's modulus to the real calcification tissues.

In the present invention, ultrasound and microbubbles are combined to generate cavitation effects. When microbubbles are infused into blood vessels, the microbubbles can be attached to target sites, followed by activation of ultrasound and generating shock waves to destroy the microbubbles. The present invention provides a method for microbubble preparation, and the microbubbles used herein are from a customized formulation: using 1,2-dipalmitoyl-sn-glycero-3-phosphocholine (DPPC), 1,2-distearoyl-sn-glycero-3-phosphoethanolamine-N-[methoxy(polyethyleneglycol)-5000](DSPE-PEG 5000), and 1,2-distearoyl-sn-glycero-3-phospho-(1'-rac-glycerol) (DSPG) at weight ratio of 2.5:1:1. The working concentration is 1000 folds dilution of the stock concentration, whereas flexible formulation ratio can be applied for different applications.

In another embodiment, the present invention provides a balloon catheter system assisted by ultrasound and microbubbles, including: a controller; a balloon catheter; at least one ultrasound transducer, and the ultrasound transducer is located within the balloon catheter, with the ultrasound transducer connected to the controller.

In another embodiment, the present invention uses external probe design, with specially designed ultrasound waveforms to conduct structure destruction study on a vessel calcification model.

In another embodiment, the present invention provides a method for vasodilation, including: providing a balloon catheter to a blood vessel; infusing microbubbles into the balloon catheter and controlling a ultrasound transducer to start working to destroy microbubble and generate shock waves; smoothly inflating the balloon catheter at the hardened portion of the blood vessel.

In another embodiment, a microbubble solution composition is provided, and including: DPPC, DSPE-PEG 5000, and DSPG at weight ratio of 2.5:1:1, and dissolving the above materials in a combination of one or more of dichloromethane, chloroform, acetonitrile, methanol, or ethyl acetate, followed by heating up and vortex mixing. In a preferred embodiment, mix DPPC of 10 mg, DSPE-PEG 5000 of 4 mg, and DSPG of 4 mg, and dissolve the above materials in chloroform and followed by heating up and vortex mixing.

The microbubble solution composition as described above is filled with a gas and then undergoes freeze-dried process.

The gas as described above is a combination of one or more of nitrogen, carbon dioxide, oxygen, or perfluorocarbon.

In order to better understand the object, efficacy, features and structure of the present invention, the following are examples of preferred embodiments and the related drawings.

DETAILED DESCRIPTION

Figure 1:
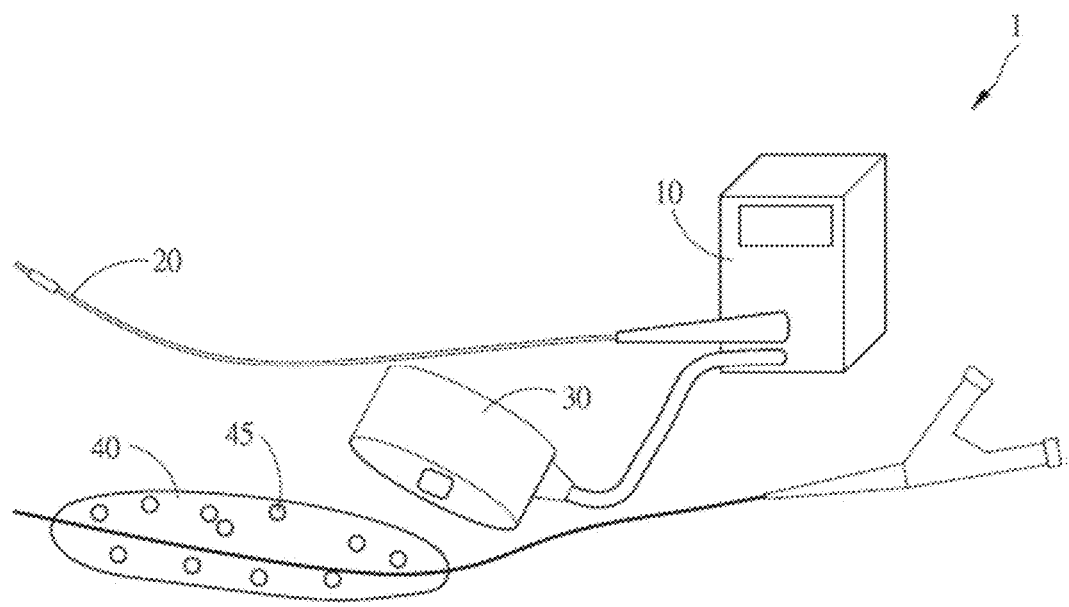
FIG. 1 is an embodiment of a balloon catheter system assisted by ultrasound and microbubbles in the present invention.
Figure 2:
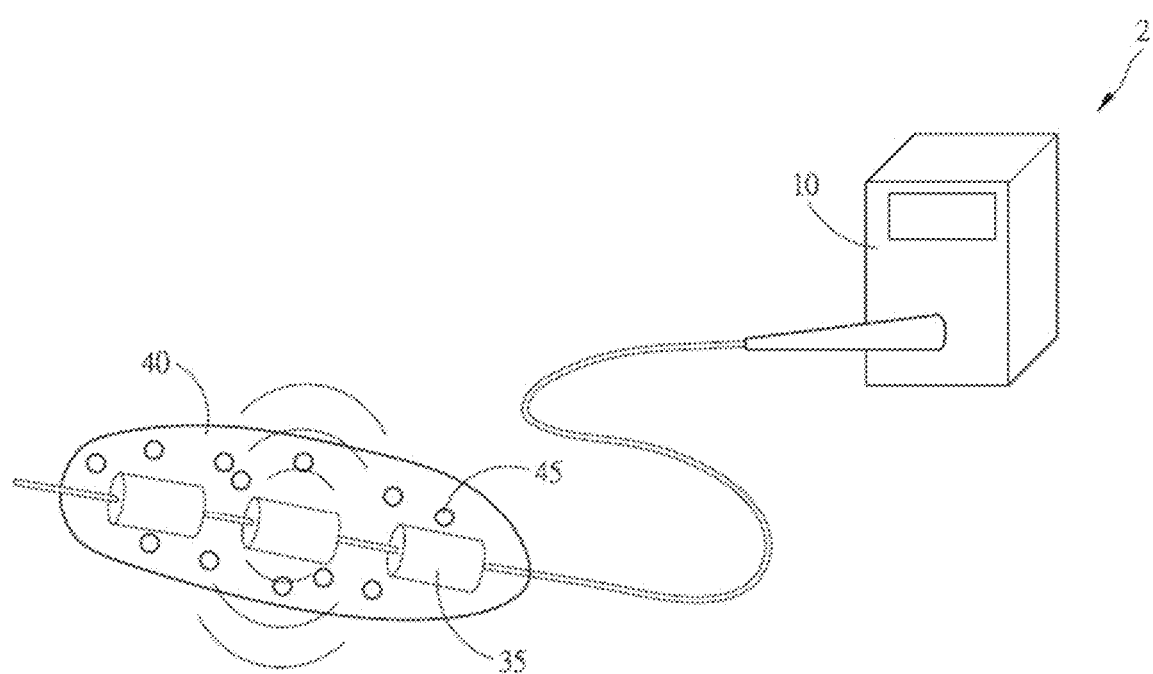
FIG. 2 is another embodiment of a balloon catheter system assisted by ultrasound and microbubbles in the present invention.

FIG. 1 and FIG. 2 are embodiments of a balloon catheter system assisted by ultrasound and microbubbles of the present invention. Please refer to FIG. 1, an embodiment of a balloon catheter system assisted by ultrasound and microbubbles 1, including: a controller 10; a sensor catheter 20; a highly focused ultrasound probe 30, and a balloon catheter 40, wherein the highly focused ultrasound probe 30 and the sensor catheter 20 are connected to the controller 10.

Please refer to FIG. 2, an embodiment of a balloon catheter system assisted by ultrasound and microbubbles 2, including: a controller 10; a balloon catheter 40; at least one ultrasound transducer 35, wherein the ultrasound transducer 35 is located within the balloon catheter 40, and the ultrasound transducer 35 is connected to the controller 10.

Figure 3:
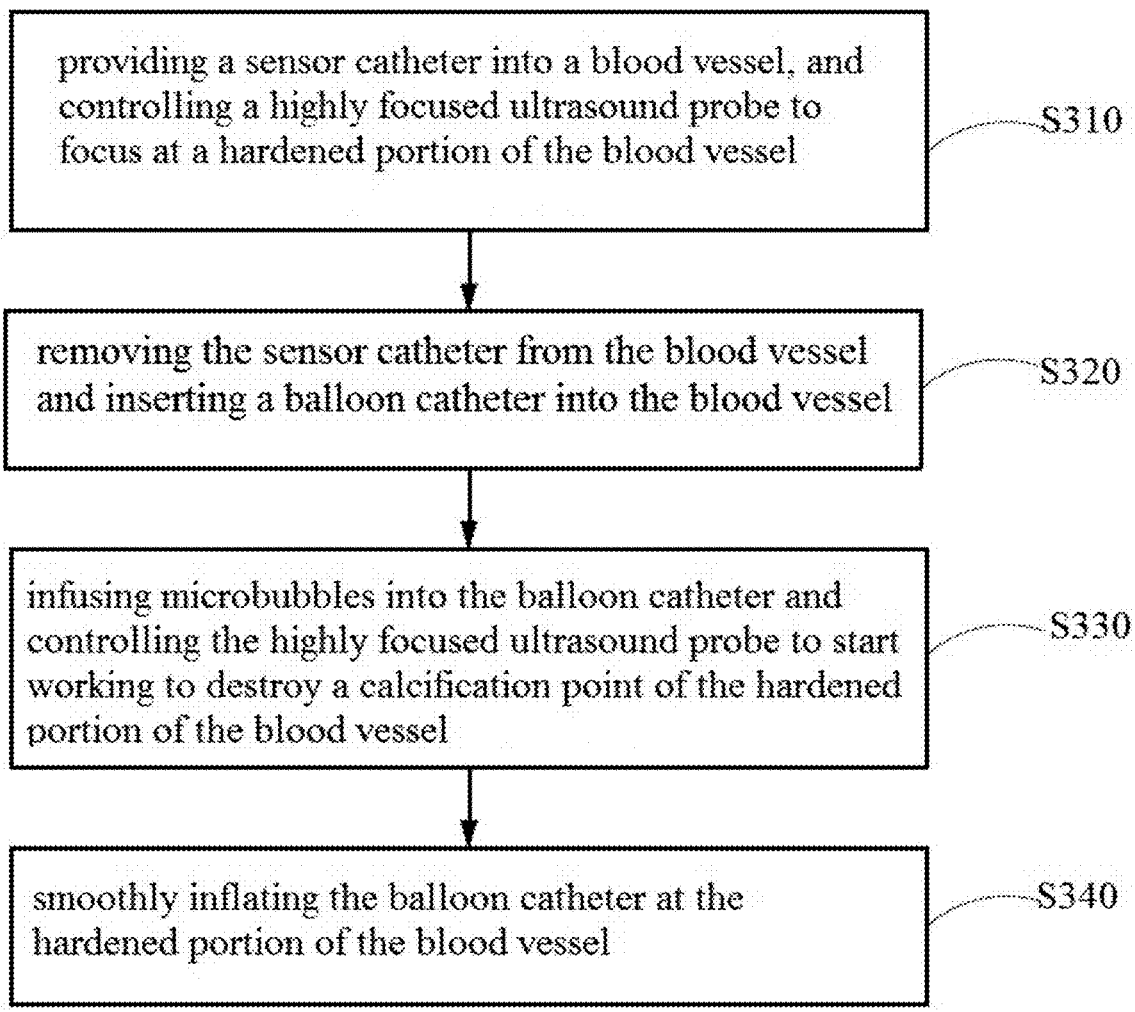
FIG. 3 is an embodiment of a method for vasodilation in the present invention.

FIG. 3. is an embodiment of a method for vasodilation. Please refer to FIG. 1 and FIG. 3, an embodiment of a method of vasodilation, including: providing a sensor catheter 20 into a blood vessel, and controlling a highly focused ultrasound probe 30 to focus at a hardened portion of the blood vessel; removing the sensor catheter 20 from the blood vessel and inserting a balloon catheter 40 into the blood vessel; infusing microbubbles 45 into the balloon catheter 40 and controlling the highly focused ultrasound probe 30 to start working to destroy a calcification point of the hardened portion of the blood vessel; smoothly inflating the balloon catheter 40 at the hardened portion of the blood vessel.

Please refer to FIG. 3, in the step S310: providing a sensor catheter into a blood vessel, and controlling a highly focused ultrasound probe to focus at a hardened portion of the blood vessel.

Please refer to FIG. 3, in the step S320: removing the sensor catheter from the blood vessel and inserting a balloon catheter into the blood vessel.

Please refer to FIG. 3, in the step S330: infusing microbubbles into the balloon catheter and controlling the highly focused ultrasound probe to start working to destroy a calcification point of the hardened portion of the blood vessel.

Please refer to FIG. 3, in the step S340: smoothly inflating the balloon catheter at the hardened portion of the blood vessel.

Figure 4:
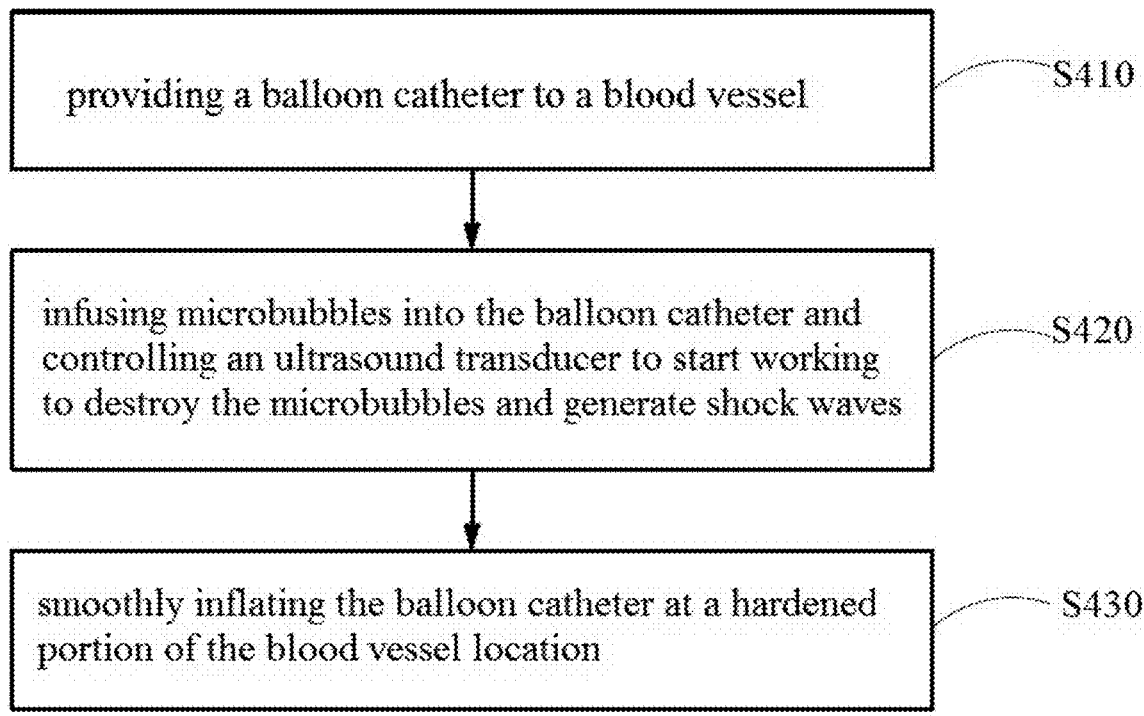
FIG. 4 is another embodiment of a method for vasodilation in the present invention.

FIG. 4. is another embodiment of a method for vasodilation. Please refer to FIG. 2 and FIG. 4, an embodiment of a method of vasodilation, including: providing a balloon catheter 40 into a blood vessel; infusing microbubbles 45 into the balloon catheter 40 and controlling a ultrasound transducer 35 to start working to destroy microbubbles 45 and generate shock waves; smoothly inflating the balloon catheter 40 at a hardened portion of the blood vessel.

Please refer to FIG. 4, in the step S410: providing a balloon catheter to a blood vessel.

Please refer to FIG. 4, in the step S420: infusing microbubbles into the balloon catheter and controlling an ultrasound transducer to start working to destroy the microbubbles and generate shock waves.

Please refer to FIG. 4, in the step S430: smoothly inflating the balloon catheter at a hardened portion of the blood vessel location.

A preferred embodiment of the present invention
Experimental Methods
Vessel Calcification Model—A General Internal Calcification Model Production of a 58.8% plaster model: mixing plaster powder and water at a weight ratio of 10:7 to form a uniform mixture, and then pouring the mixture into a mold, followed by incubation of the mixture in an oven for 20 minutes for solidification. Next, measuring the Young's modulus of the solidified plaster model and examining whether the plaster model has similar Young's modulus (elasticity) to the real vessel calcification tissues. The results are shown in the Table 1 below.

Measurement results of a general internal calcification model:

| Items | Thickness (mm) | Young's modulus (GPa) |
|---|---|---|
| Glass (standard) | 4.8 | 82.13 |
| Model 1 | 2.8 | 12.29 |
| Model 2 | 2.57 | 12.27 |
| Model 3 | 2.94 | 20.23 |

The measurement results show that the Young's modulus of the commonly seen vessel calcification tissues is 20-40 GPa. The plaster model produced in this experiment has Young's modulus similar to the commonly seen vessel calcification tissues.

Vessel Calcification Model—A Heavy Calcification Model

Production of an 80.6% plaster model: mixing plaster powder and water at a weight ratio of 25:6 to form a uniform mixture, and then pouring the mixture into a mold, followed by waiting the mixture for 20 minutes for solidification. Next, measuring the Young's modulus of the solidified plaster model and examining whether the plaster model has similar Young's modulus (elasticity) to the real vessel heavy calcification tissues. The results are shown in the Table 2 below.

Measurement Results of a Heavy Calcification Model:

| Items | Thickness (mm) | Young's modulus (GPa) |
|---|---|---|
| Model 1 | 3 | 133.81 |
| Model 2 | 2.6 | 113.85 |
| Model 3 | 2.6 | 116.09 |

The measurement results show that the Young's modulus of the commonly seen heavy vessel calcification tissues is 110-130 GPa. The plaster model produced in this experiment has Young's modulus similar to the commonly seen heavy vessel calcification tissues.

Figure 5:
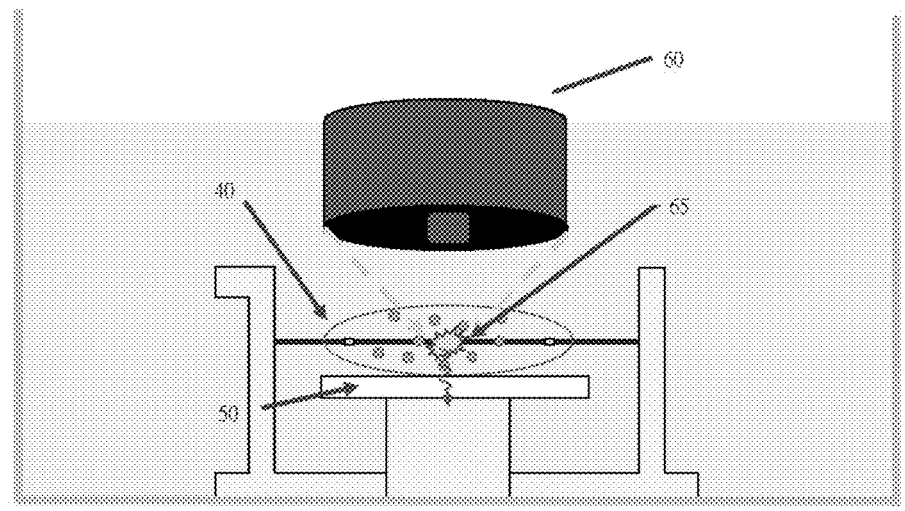
FIG. 5 is an experimental setup for a vessel calcification model in the present invention.

Please refer to FIG. 5, a vessel calcification model in the present invention. For applying internal probe design or external probe design, a general internal calcification model 50 is made with 58.8% plaster (thickness: 3 mm) and has Young's modulus of 12.3 GPa; a heavy calcification model 50 is made with 80.6% plaster (thickness: 3 mm) and has Young's modulus of 110-130 GPa. Lipid microbubbles (40.6*$10^6$ MBs/mL) are infused into a balloon catheter 40, followed by ultrasound insonation 60 at 1.5 MHz for 30 minutes, ultrasound and microbubbles are combined to generate cavitation effects 65.

Figure 6:
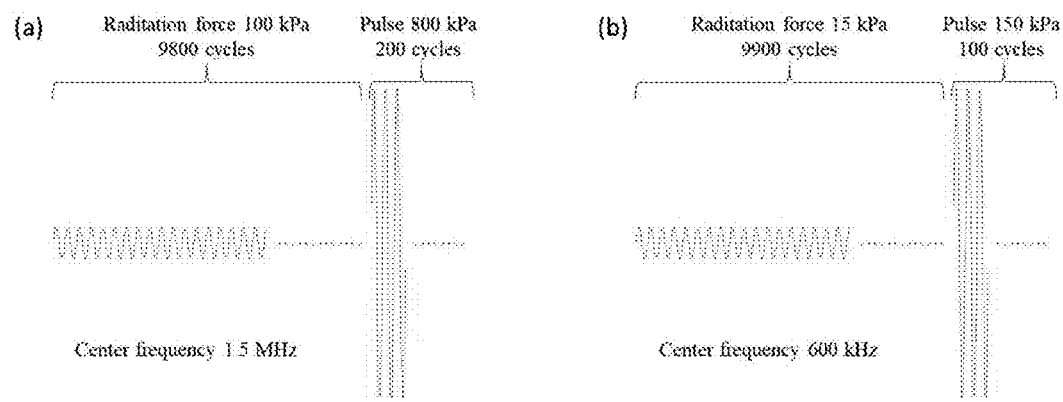
FIG. 6 is a diagram of specially designed ultrasound waveforms in the present invention.

Please refer to FIG. 6(*a*), a specially designed ultrasound waveforms in the present invention. Using radiation force pulses with center frequency of 1.5 MHz, pressure of 100 kPa, and duty cycles of 98%, to push lipid microbubbles to the internal surface of the balloon catheter.

Next, applying destruction pulses with center frequency of 1.5 MHz, pressure of 800 kPa, and duty cycles of 2%, to generate cavitation. Using a 20 MHz C-Scan imaging system to image the plaster model before and after ultrasound insonation, and drawing the difference.

In another embodiment, please refer to FIG. 6(*b*), a specially designed ultrasound waveforms in the present invention. Using radiation force pulses with center frequency of 600 kHz, pressure of 15 kPa, and duty cycles of 99%, to deliver lipid microbubbles to the internal surface of the balloon catheter.

Next, applying destruction pulses with center frequency of 600 kHz, pressure of 150 kPa, and duty cycles of 1%, to generate cavitation. Using a 20 MHz C-Scan imaging system to image the plaster model before ultrasound insonation and after ultrasound insonation, and drawing the difference.

Microbubbles Preparation

Steps for microbubbles preparation are as follows: a composition of the microbubbles is created by using three materials of DPPC, DSPE-PEG 5000, and DSPG at a weight ratio of 2.5:1:1 (DPPC:DSPE-PEG5000:DSPG). The average diameter after preparation is 2±0.5 μm. The stock concentration is about 40*$10^9$ microbubbles/mL (MB s/mL). In the experiments, the microbubbles are further diluted before use.

In an embodiment, the composition is: DPPC of 10 mg, DSPE-PEG 5000 of 4 mg, and DSPG of 4 mg.

Accurately weighing and dissolving the three materials in 1 mL of chloroform as a solvent, sonicating and mixing under heating with an ultrasonic sonicator. A uniform and transparent solution is finished.

Dividing the above solution into several 1.5 mL vials with 250 μL solution in each vial, drying the solution with heating in a 65° C. waterbath for 30 minutes, followed by vacuum overnight to reach complete removal of the solvent.

Next, dissolving 0.1 g of glycerin in 20 mL of phosphate buffered saline (PBS), and taking 800 μL into the above vial. Sitting the vial at 65° C. waterbath for 5 minutes, followed by mixing the solution with a ultrasonic sonicator and vacuuming to remove gas that is dissolved in the water phase of the solution. After degassing, adding perfluoropropane ($C_3F_8$) into the vial and sonicating for 45 seconds. During sonication, lipids will form microbubbles due to surface tension, and these microbubbles are used in the present invention.

Figure 7:
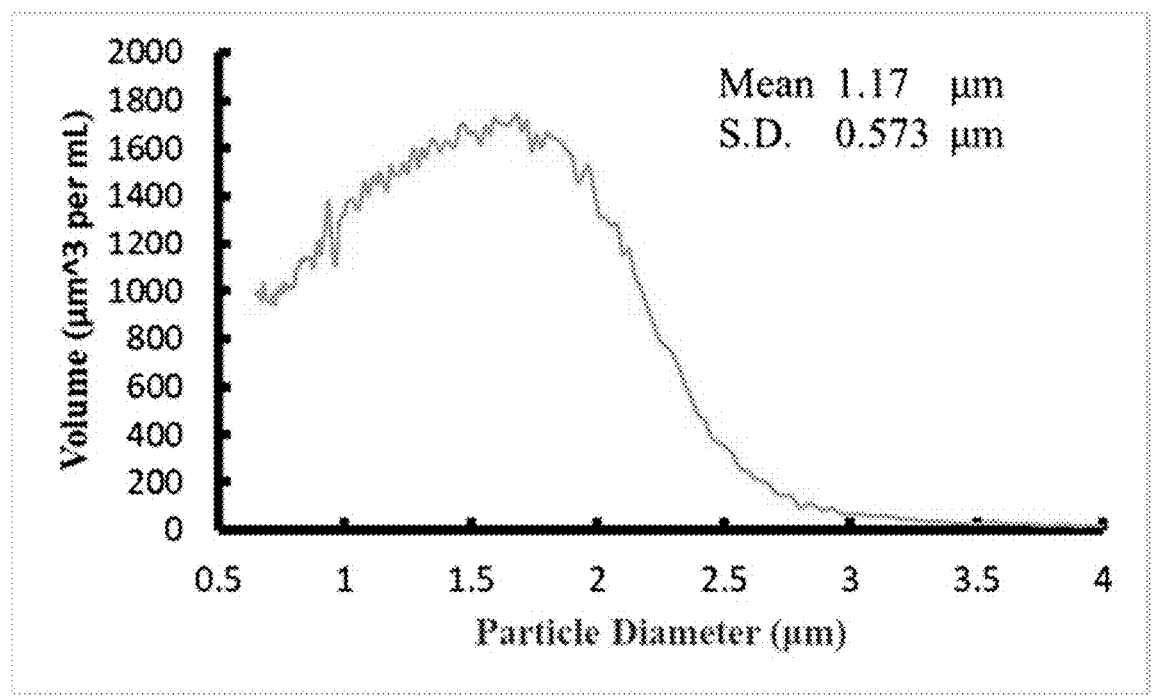
FIG. 7 is a diagram of size distribution of self-made microbubbles prepared in the present invention.

Please refer to FIG. 7, a diagram of size distribution of the microbubbles prepared in the present invention.

Example 1

Feasibility Study of the External Probe Design—Part A

Please refer to FIG. 5 for experimental setup. The probe is movable. During the feasibility study, it just requires confirming that such setup can effectively destroy the calcification model. Therefore, a planar general internal calcification model is selected to examine ultrasound's effect on it. The experimental setup is as follows:

Probe: 1.5 MHz ultrasound transducer
Balloon catheter: Regular PTA balloon catheter
Microbubbles: The self-made microbubbles with 1000 folds of dilution After a series of tests, a special ultrasound waveform is designed to examine feasibility of this setup. The specially designed ultrasound waveform is described in FIG. 6(*a*). The study contains three groups (A, B, and C):

A. US with radiation force+MB (abbreviated as: US w/RF+MB).

The experimental protocol is as follows:
  a. Infuse microbubbles into the balloon catheter.
  b. Insonate with 1.5 MHz ultrasound for 10 minutes. First, apply 9800 cycles of lower-amplitude ultrasound to create radiation force, to push the microbubbles to the internal surface of the balloon catheter. Then, apply 200 cycles of higher-amplitude ultrasound to create destruction force. The microbubbles are destroyed due to the amplitude change, thus generating cavitation effects and resulting in strong shock waves, eventually destroying the calcification structure.

B. US without radiation force+MB (abbreviated as: US w/o RF+MB).

The experimental protocol is as follows:
  a. Infuse microbubbles into the balloon catheter.
  b. Insonate with 1.5 MHz ultrasound for 10 minutes. In this group, radiation force is not used. The whole process only applies 200 cycles of higher-amplitude ultrasound to create destruction force. The microbubbles are destroyed due to the amplitude change, thus generating cavitation effects and resulting in strong shock waves, eventually destroying the calcification structure.

C. US without radiation force (abbreviated as: US only).

The experimental protocol is as follows:
  a. Insonate with 1.5 MHz ultrasound for 10 minutes. This is a control group with only 200 cycles of higher-amplitude ultrasound, to test the destruction force to the calcification model without existence of radiation force and microbubbles.

Results of the Feasibility Study of the External Probe Design, Part A

Figure 8:
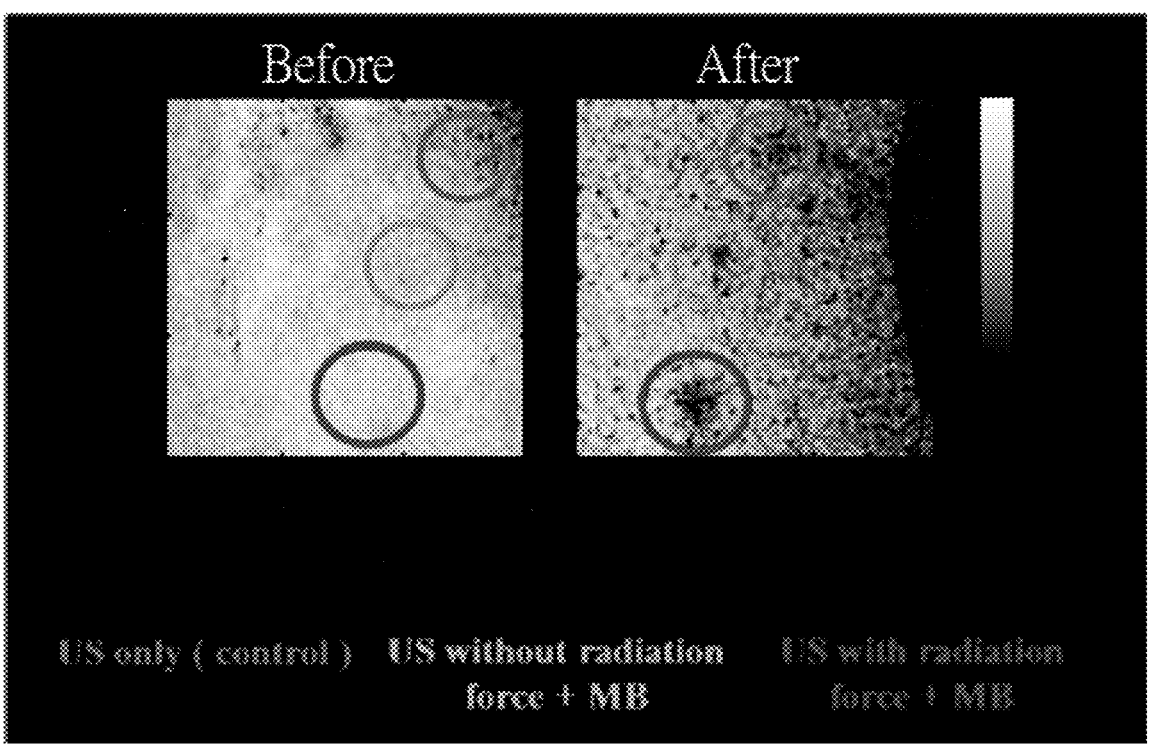
FIG. 8 shows results of a feasibility study of an external probe design in the present invention—part A.

Please refer to FIG. 8, the scanning results of the planar vessel calcification model generated by the 20 MHz C-Scan imaging system, before and after ultrasound insonation. Comparing with the group without radiation force (B, US w/o RF+MB) and control (C, US only), the group with radiation force (A, US w/ RF+MB) demonstrates better destruction results.

Figure 9:
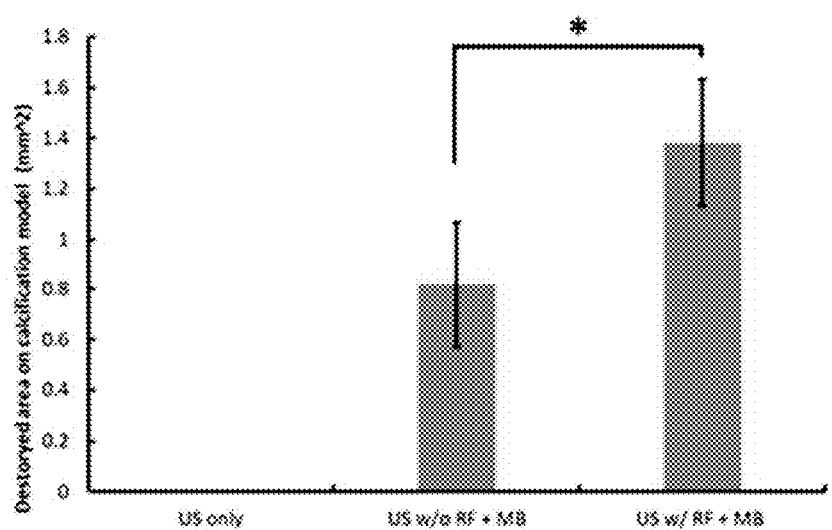
FIG. 9 shows a quantitative analysis of the results of the feasibility study of the external probe design in the present invention—part A.

Using the intensity level before ultrasound insonation as baseline, the intensity difference is calculated before and after ultrasound insonation, and the area with difference higher than 10 dB is labeled as quantification of destruction of the plaster model. Please refer to FIG. 9, quantitative results of the destruction area of every group. The group with radiation force (A group) has destruction area of 1.4 mm$^2$, whereas the group without radiation force (B group) has destruction area of 0.8 mm$^2$, demonstrating radiation force increases destruction for 68% ($p<0.05$). The method in the present invention can successfully destroy calcification and thus assisting inflation of balloon catheters. In the clinical practice, we will design balloon catheters with internal probes, in order to control ultrasound insonation more accurately during inflation of balloon catheters.

Example 2

Feasibility Study of the External Probe Design—Part B

Please refer to FIG. 5 for experimental setup. The probe is movable. During the feasibility study, it just requires confirming that such setup can effectively destroy the calcification model. Therefore, a planar general internal calcification model is used to examine ultrasound's effect thereon. The experimental setup is as follows:

Probe: 600 kHz ultrasound transducer

Microbubbles: The self-made microbubbles with 100 folds of dilution

After a series of tests, a special ultrasound waveform is designed to examine the feasibility of this setup. The specially designed ultrasound waveform is described in FIG. 6(*b*). The study contains three groups (A, B, and C):

A. US with radiation force+MB (abbreviated as: US w/ RF+MB).

The experimental protocol is as follows:
  a. Infuse microbubbles into the balloon catheter.
  b. Insonate with 600 kHz ultrasound for 10 minutes. First, apply 9900 cycles of lower-amplitude ultrasound to create radiation force, to push the microbubbles to the internal surface of the balloon catheter. Then, apply 100 cycles of higher-amplitude ultrasound to create destruction force. The microbubbles are destroyed due to the amplitude change, thus generating cavitation effects and resulting in strong shock waves, eventually destroying the calcification structure.

B. US without radiation force+MB (abbreviated as: US w/o RF+MB).

The experimental protocol is as follows:
  a. Infuse microbubbles into the balloon catheter.
  b. Insonate with 600 kHz ultrasound for 10 minutes. In this group, radiation force is not used. The whole process only applies 100 cycles of higher-amplitude ultrasound to create destruction force. The microbubbles are destroyed due to the amplitude change, thus generating cavitation effects and resulting in strong shock waves, eventually destroying the calcification structure.

C. US without radiation force (abbreviated as: US only).

The experimental protocol is as follows:
  a. Insonate with 600 kHz ultrasound for 10 minutes. This is a control group with only 100 cycles of higher-amplitude ultrasound, to test the destruction force to the calcification model without existence of radiation force and microbubbles.

Results of the Feasibility Study of the External Probe Design, Part B

Figure 10:
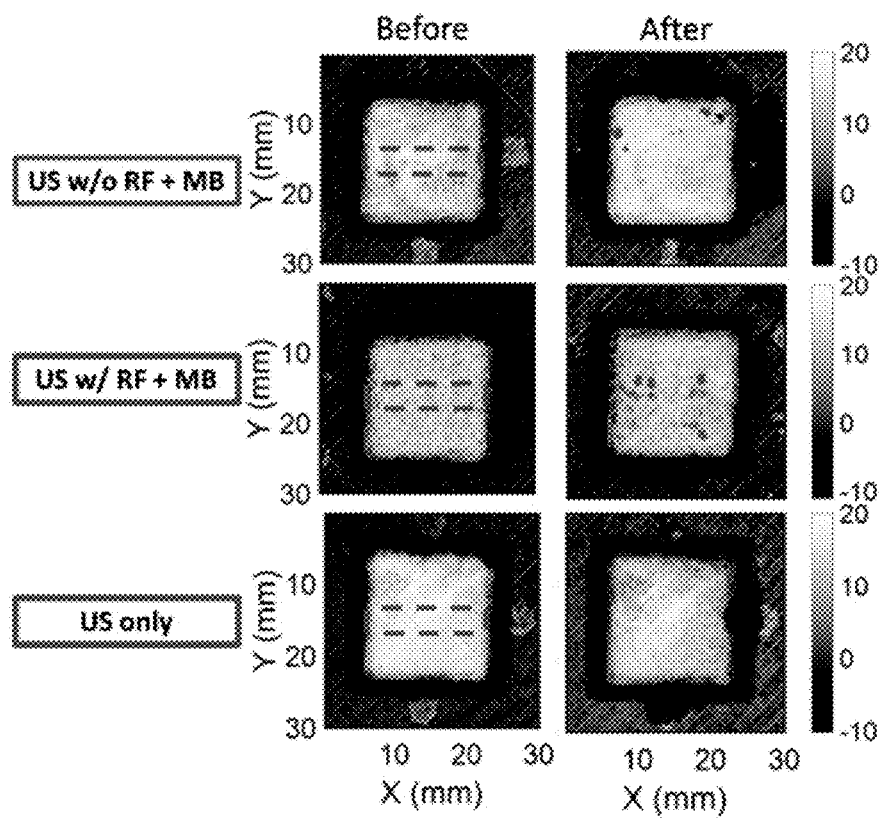
FIG. 10 shows results of the feasibility study of the external probe design in the present invention—part B.

Please refer to FIG. 10, the scanning results of the planar vessel calcification model generated by the 20 MHz C-Scan imaging system, before and after ultrasound insonation. Comparing with the group without radiation force (B, US w/o RF+MB) and control group (C, US only), the group with radiation force (A, US w/ RF+MB) demonstrates better destruction results.

Example 3

Feasibility Study of the External Probe Design—Part C

After planar vessel calcification models, this experiment focuses on tubular vessel calcification models and tests whether such experimental setup can help destroy tubular vessel calcification models. Production of the tubular vessel calcification models is similar to the methods in "Feasibility study of the external probe design, part A", with the only difference on the mold. By 3-D printing the appropriate molds, a tubular general internal calcification model (thickness 3 mm) is made to mimic the most common calcification in the blood vessels—superficial calcific sheet.

Figure 11:
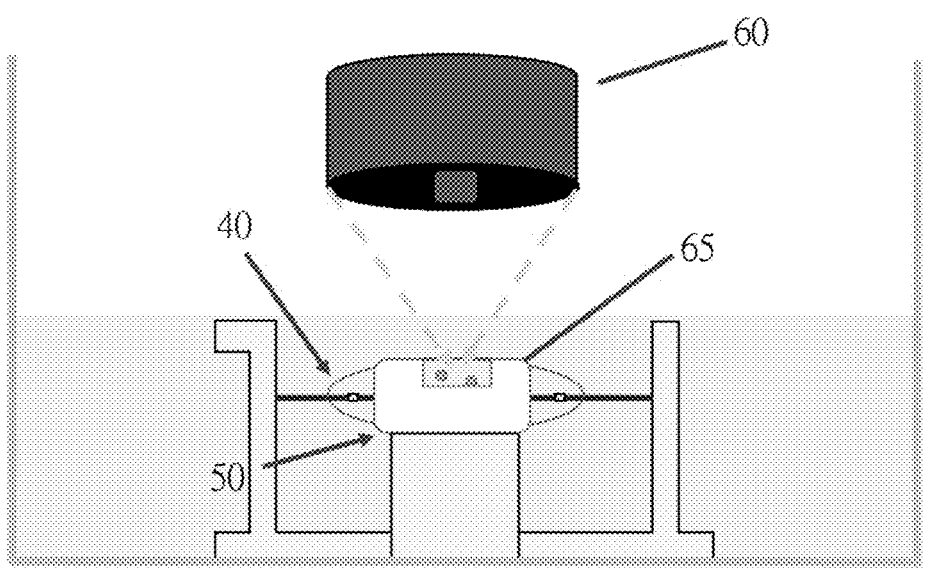
FIG. 11 is an experimental setup of the feasibility study of the external probe design in the present invention—part C.

Please refer to FIG. 11 for experimental setup. The experimental protocol is as follows:
  a. For both experimental group (with ultrasound insonation 60) and control group (without ultrasound insonation), put tubular calcification models 50 onto balloon catheters 40.

b. Infuse microbubbles into the balloon catheter 40.
c. In the experimental group, apply ultrasound insonation 60 with the specially designed ultrasound waveforms used in the "Feasibility study of the external probe design, part A", for 10 minutes. No ultrasound insonation is applied in the control group.
d. Inflate balloon catheters and monitor the pressure that the tubular vessel calcification model 50 starts to break.

Results of the Feasibility Study of the External Probe Design, Part C

Experimental group: The tubular vessel calcification model starts to break at pressure of 6 atm.

Control group: The tubular vessel calcification model starts to break at pressure of 8 atm.

The results for the feasibility study of the external probe design part C demonstrate that the shock waves induced by cavitation effects achieved by ultrasound and microbubbles can reduce the inflation threshold that the tubular vessel calcification model starts to break, i.e., ultrasound and microbubbles can successfully achieve the destruction effects on the tubular vessel calcification model.

Example 4

When blood vessels are small and cannot produce sufficient echo signals for focusing of ultrasound, this present invention uses a sensor catheter to assist focusing of ultrasound on the disease site. The treatment protocol is as follows:
a. Insert the sensor catheter into a blood vessel. With the guidance of the sensor catheter, focus ultrasound on the disease site.
b. Remove the sensor catheter from the blood vessel and insert a balloon catheter into the blood vessel.
c. Infuse microbubbles into the balloon catheter and apply ultrasound insonation to destroy the calcification tissues.
d. Inflate the balloon catheter and finish the treatment.

Example 5

Figure 12:
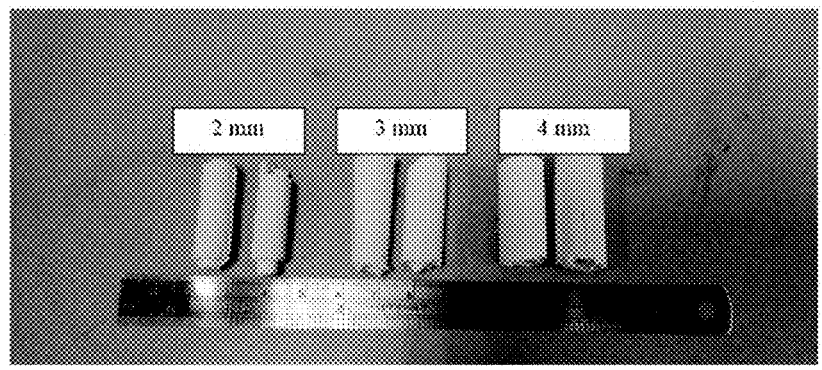
FIG. 12 shows tubular vessel calcification models with three thicknesses for an internal probe design in the present invention.

Feasibility Study of the Internal Probe Design—Vessel Calcification Model with Varies Thickness The setup of the internal probe design uses the ultrasound transducers made from the piezoelectric tubes purchased from PI (Ceramic GmbH, Lederhose, Germany), plus tubular vessel calcification models, to examine whether or not the inflation threshold of the tubular vessel calcification models can be reduced. The inflation threshold is the pressure where the tubular vessel calcification model starts to break. Please refer to FIG. 12, this study applies tubular general internal vessel calcification models with three thicknesses for test: 2 mm, 3 mm, and 4 mm thickness.

Figure 13:
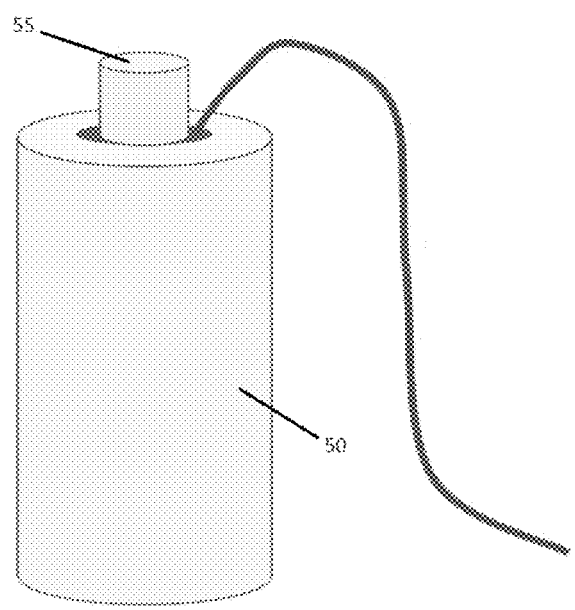
FIG. 13 is an experimental setup of the feasibility study of the internal probe design in the present invention.

The experimental protocol is as follows:
Please refer to FIG. 13, an experimental setup of the feasibility study of the internal probe design in the present invention:
a. Place both the experimental and control group vessel calcification models 50 in water.
b. Infuse microbubbles into the lumen of the vessel calcification model 50 in the experimental group. Place a tubular ultrasound transducer 55 in the lumen and start ultrasound insonation with specially designed ultrasound waveforms for 20 minutes, please refer to FIG. 6(*a*). In the control group, no ultrasound transducer 55 is used.
c. Take the experimental and control group vessel calcification models 50 out of water, insert a balloon catheter, increase water pressure and monitor the pressure where the tubular vessel calcification model 50 starts to break.

Results:
Table 3 shows that results of feasibility study of the internal probe design—vessel calcification model with varies thickness.

|  | 2 mm | 3 mm | 4 mm |
| --- | --- | --- | --- |
| Control group | 4 atm | 7 atm | 9 atm |
| Experimental group (ultrasound) | 4 atm | 4 atm | 7 atm |

Example 6

Feasibility Study of the Internal Probe Design—Ultrasound Insonation Time

The setup of the internal probe design uses the ultrasound transducers made from the piezoelectric tubes purchased from PI, plus tubular vessel calcification models, to examine whether or not the inflation threshold of the tubular vessel calcification models can be reduced. In addition, to evaluate the more truthful effects in heavily calcified tissues, this study applies a tubular heavy calcification model with thickness of 3 mm.

The Experimental Protocol is as Follows:
Please refer to FIG. 14, an experimental setup of the feasibility study of the internal probe design in the present invention:
a. Place both the experimental and control group vessel calcification models 50 in water. Experimental group: Place a tubular ultrasound transducer 55 in the lumen of the tubular heavy calcification model 50, followed by applying ultrasound only (US only) or applying ultrasound plus microbubbles (US+MBs). Control group: Neither ultrasound nor microbubbles is used (Untreated).
b. Infuse microbubbles into the lumen of the vessel calcification model 50 in the experimental group, with a flow rate of 144 mL/hr. Apply ultrasound insonation with the following parameters: frequency: 600 kHz, pressure: 300 kPa, cycles: 100, pulse repetition rate (PRF): 1 Hz, microbubble concentration: 100 folds dilution of the stock solution ($40*10^9$ MBs/mL), insonation duration: 10-30 minutes.
c. Take the experimental and control group vessel calcification models 50 out of water, insert a balloon catheter, increase water pressure and monitor the pressure where the tubular vessel calcification model 50 starts to break.

Figure 15:
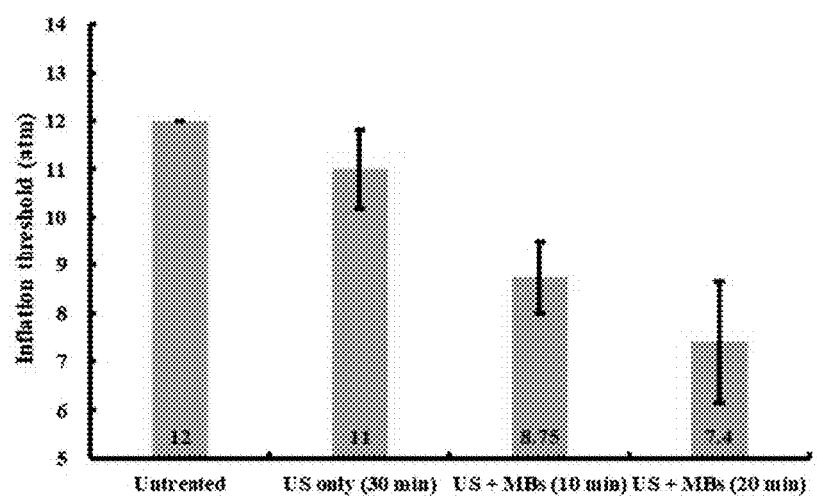
FIG. 15 shows results of the feasibility study of the internal probe design in the present invention—ultrasound insonation time.

Results:
Please refer to FIG. 15, results of the feasibility study of the internal probe design—ultrasound insonation time. The group without ultrasound and microbubbles (Untreated) has an inflation threshold of higher than 12 atm; the group with ultrasound only (US only) has an inflation threshold of 11 atm; the group of combining ultrasound and microbubbles with insonation of 10 minutes (US+MBs (10 min)) has an inflation threshold of 8.75 atm; and the group of combining ultrasound and microbubbles with insonation of 20 minutes (US+MBs (20 min)) has an inflation threshold of 7.4 atm.

Example 7

Feasibility Study of the Internal Probe Design—Ultrasound Cycles

The setup of the internal probe design uses the ultrasound transducers made from the piezoelectric tubes purchased from PI, plus tubular vessel calcification models, to examine whether or not the inflation threshold of the tubular vessel calcification models can be reduced. This study applies a tubular heavy calcification model with thickness of 3 mm.

Figure 14:
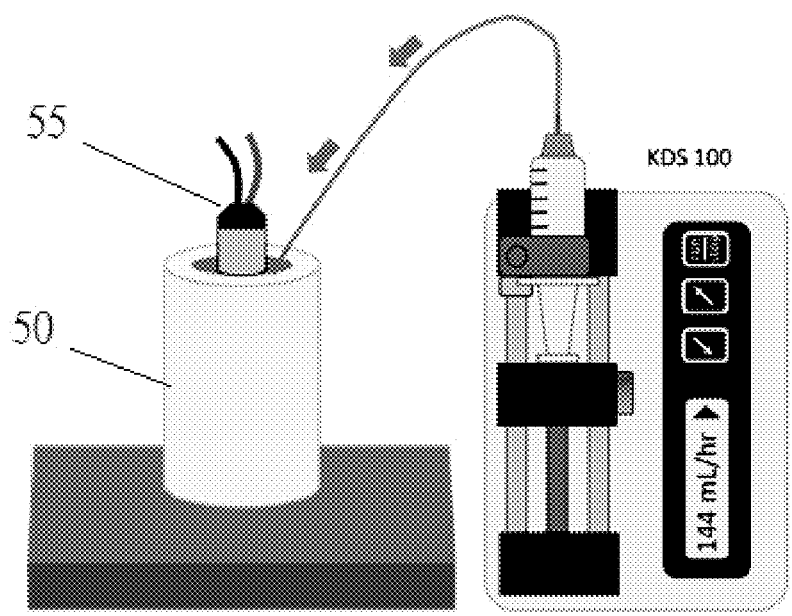
FIG. 14 is an experimental setup of the feasibility study of the internal probe design in the present invention.

The Experimental Protocol is as Follows:

Please refer to FIG. 14, an experimental setup of the feasibility study of the internal probe design in the present invention:
- a. Place the vessel calcification models 50 in water. Then, place a tubular ultrasound transducer 55 in the lumen of the tubular heavy calcification model 50.
- b. Infuse microbubbles into the lumen of the vessel calcification model 50 in the experimental group, with a flow rate of 144 mL/hr. Apply ultrasound insonation with the following parameters: frequency: 600 kHz, pressure: 300 kPa, cycles: 10-1000, PRF: 1 Hz, microbubble concentration: 100 folds dilution of the stock solution ($40*10^9$ MBs/mL), insonation duration: 20 minutes.
- c. Take the vessel calcification models 50 out of water, insert a balloon catheter, increase water pressure and monitor the pressure where the tubular vessel calcification model 50 starts to break.

Figure 16:
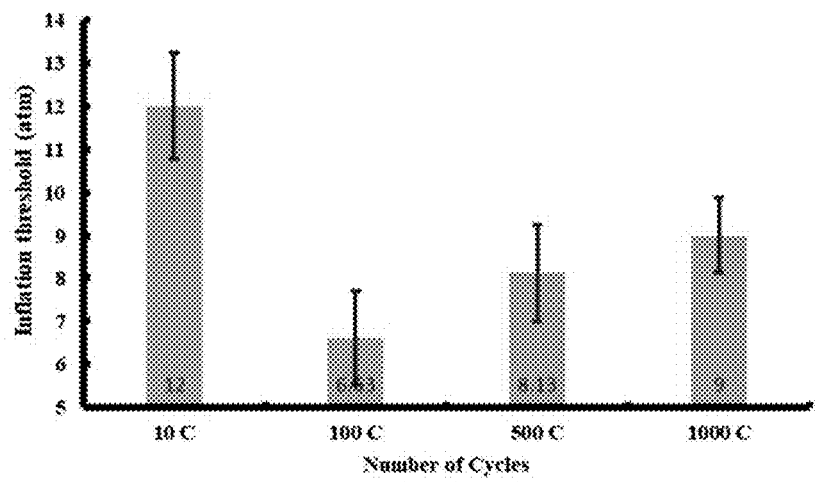
FIG. 16 shows results of the feasibility study of the internal probe design in the present invention—ultrasound cycles.

Results:

Please refer to FIG. 16, results of the feasibility study of the internal probe design—ultrasound cycles. The inflation threshold for 10, 100, 500, and 1000 cycles are 12, 6.63, 8.13, and 9 atm, respectively.

Example 8

Feasibility Study of the Internal Probe Design—Microbubble Concentration

The setup of the internal probe design uses the ultrasound transducers made from the piezoelectric tubes purchased from PI, plus tubular vessel calcification models, to examine whether or not the inflation threshold of the tubular vessel calcification models can be reduced. This study applies a tubular heavy calcification model with thickness of 3 mm.

The Experimental Protocol is as Follows:

Please refer to FIG. 14, an experimental setup of the feasibility study of the internal probe design in the present invention:
- a. Place the vessel calcification models 50 in water. Then, place a tubular ultrasound transducer 55 in the lumen of the tubular heavy calcification model 50.
- b. Infuse microbubbles into the lumen of the vessel calcification model 50 in the experimental group, with a flow rate of 144 mL/hr. Apply ultrasound insonation with the following parameters: frequency: 600 kHz, pressure: 300 kPa, cycles: 100, PRF: 1 Hz, microbubble concentration: 75, 100, or 200 folds dilution of the stock solution ($40*10^9$ MBs/mL), plus a group without microbubbles. Insonation duration: 20 minutes.
- c. Take the vessel calcification models 50 out of water, insert a balloon catheter, increase water pressure and monitor the pressure where the tubular vessel calcification model 50 starts to break.

Figure 17:
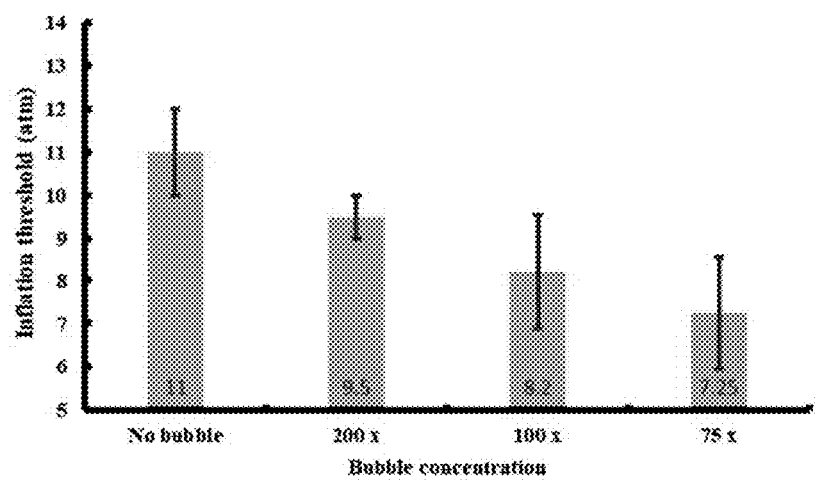
FIG. 17 shows results of the feasibility study of the internal probe design in the present invention—microbubble concentration.

Results:

Please refer to FIG. 17, results of the feasibility study of the internal probe design—microbubble concentration. The inflation threshold for 75, 100, 200 folds dilution, and without microbubbles are 7.25, 8.2, 9.5, and 11 atm, respectively.

Example 9

Feasibility Study of the Internal Probe Design—Acoustic Pressure

The setup of the internal probe design uses the ultrasound transducers made from the piezoelectric tubes purchased from PI, plus tubular vessel calcification models, to examine whether or not the inflation threshold of the tubular vessel calcification models can be reduced. This study applies a tubular heavy calcification model with thickness of 3 mm.

The Experimental Protocol is as Follows:

Please refer to FIG. 14, an experimental setup of the feasibility study of the internal probe design in the present invention:
- a. Place the vessel calcification models 50 in water. Then, place a tubular ultrasound transducer 55 in the lumen of the tubular heavy calcification model 50.
- b. Infuse microbubbles into the lumen of the vessel calcification model 50 in the experimental group, with a flow rate of 144 mL/hr. Apply ultrasound insonation with the following parameters: frequency: 600 kHz, pressure: 150, 200, 300 kPa, cycles: 100, PRF: 1 Hz, microbubble concentration: 100 folds dilution of the stock solution ($40*10^9$ MBs/mL). Insonation duration: 20 minutes.
- c. Take the vessel calcification models 50 out of water, insert a balloon catheter, increase water pressure and monitor the pressure where the tubular vessel calcification model 50 starts to break.

Figure 18:
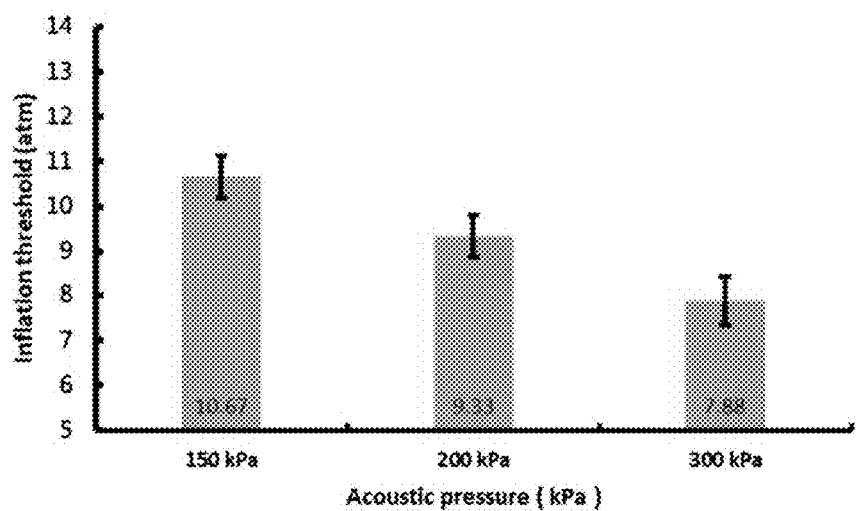
FIG. 18 shows results of the feasibility study of the internal probe design in the present invention—acoustic pressure.

Results:

Please refer to FIG. 18, results of the feasibility study of the internal probe design—acoustic pressure. The inflation threshold for 150, 200, and 300 kPa, are 10.67, 9.33, and 7.88 atm, respectively.

Example 10

Egg Shell Study

The setup of the egg shell study uses the ultrasound transducers made from the piezoelectric tubes purchased from PI. Ultrasound insonation is applied within the egg shells to generate shock waves from inside of the egg shells, followed by observation of cracks on the surface of the egg shell and evaluate the efficacy of shock waves on the biological calcification.

Figure 19:
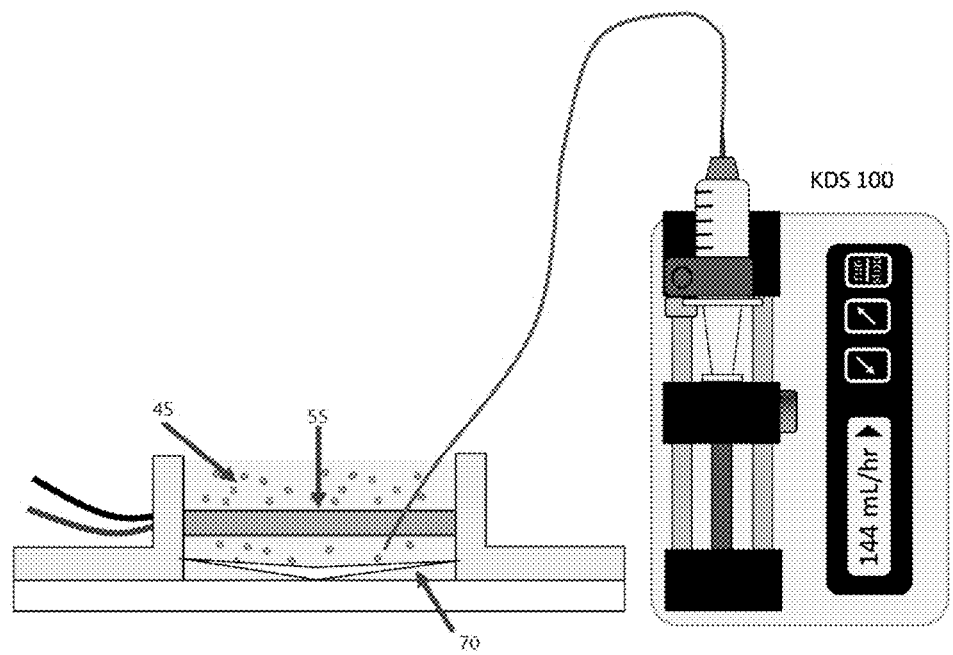
FIG. 19 is an experimental setup applied to an egg shell.

The Experimental Protocol is as Follows:

Please refer to FIG. 19, an experimental setup of the egg shell study in the present invention:
- a. Prepare an egg shell 70 and place a tubular ultrasound transducer 55 parallel to the egg shell 70.
- b. In the experimental group (with microbubbles), infuse microbubbles 45 to the surrounding area of the egg shell 70, with a flow rate of 144 mL/hr. Apply ultrasound insonation with the following parameters: frequency: 600 kHz, pressure: 300 kPa, cycles: 100, PRF: 1 Hz, microbubble concentration: 100 folds dilution of the stock solution ($40*10^9$ MBs/mL). Insonation duration: 20 minutes. The control group is applied for the same parameters without using microbubbles 45.

c. Stain the egg shells 70 with Evans Blue dye to enhance the cracks. Observation the cracks under a microscope.

Figure 20:
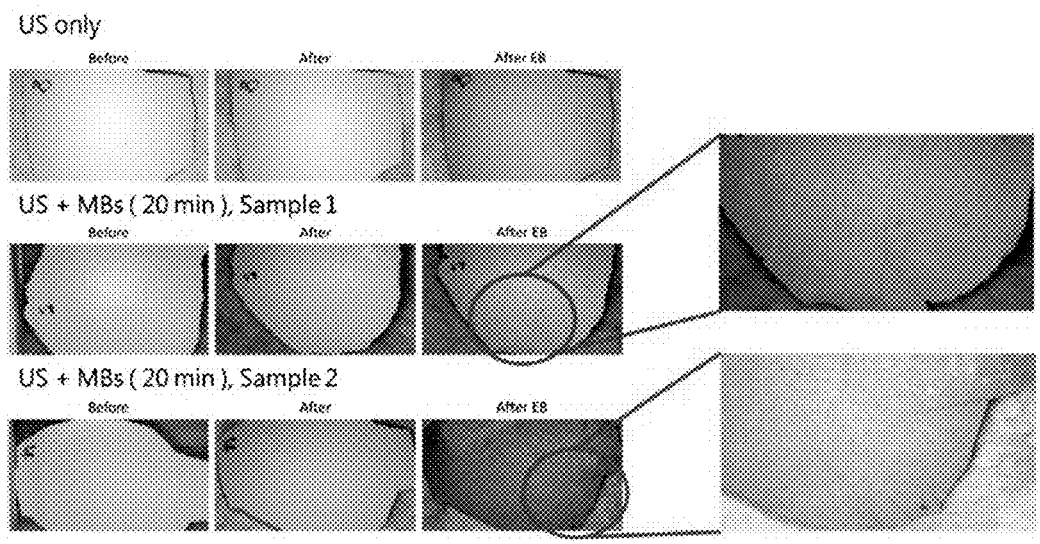
FIG. 20 shows results of FIG. 19.

Results:

Please refer to FIG. 20, results of the egg shell study. Cracks are not observed in the control group (US only), whereas obvious cracks are found in the experimental group (US+MBs (20 min)).

Example 11

Biological Effects (Using a Pig Artery)

Biological effects of ultrasound insonation is evaluated with a pig artery. The setup of the study uses the ultrasound transducers made from the piezoelectric tubes purchased from PI. Ultrasound insonation is applied at the endothelium of the pig artery, to investigate the biological effects of ultrasound shock waves in a blood vessel.

Figure 21:
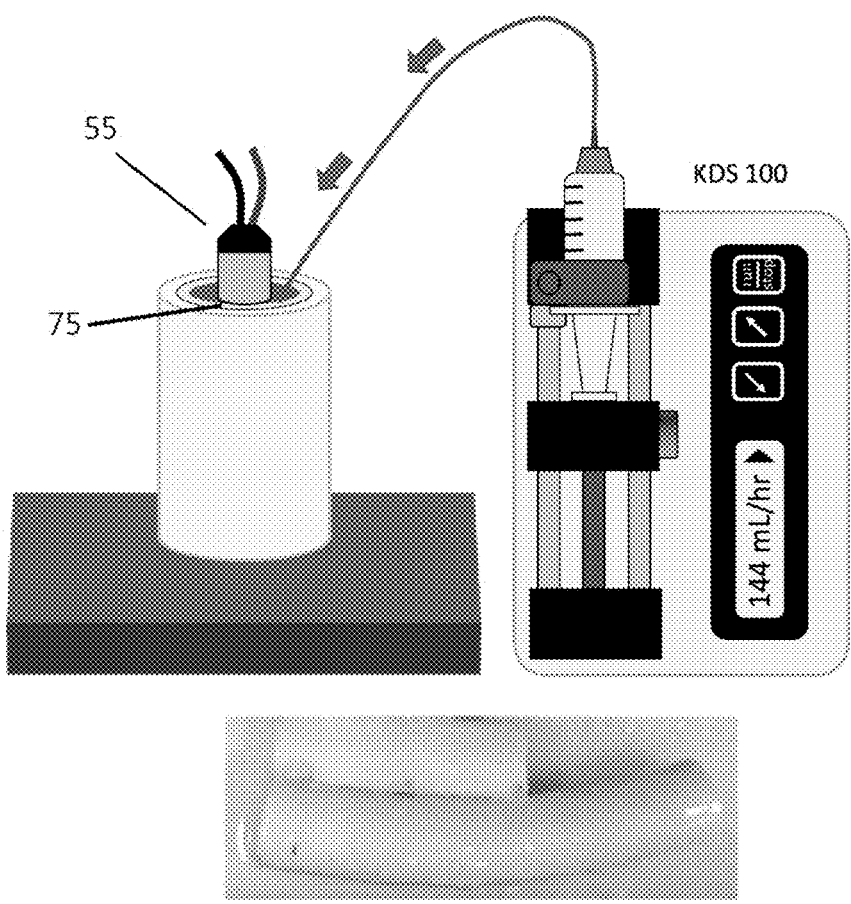
FIG. 21 is an experimental setup applied to a pig artery.

The experimental protocol is as follows:

Please refer to FIG. 21, an experimental setup of the biological effects study in the present invention:
  a. Prepare a pig artery 75 and place a tubular ultrasound transducer 55 inside the pig artery 75.
  b. In the experimental group (ultrasound plus microbubbles, US+MBs), infuse microbubbles to the lumen of the pig artery 75, with a flow rate of 144 mL/hr. Apply ultrasound insonation with the following parameters: frequency: 600 kHz, pressure: 300 kPa, cycles: 100, PRF: 1 Hz, microbubble concentration: 100 folds dilution of the stock solution ($40*10^9$ MBs/mL). Insonation duration: 20 minutes. The control groups are as follows: using ultrasound insonation only (US only), using microbubbles only (MBs only), neither ultrasound insonation nor microbubbles (Untreated).
  c. Remove the tubular ultrasound transducer 55 and analyze histopathology of the pig artery 75 under a microscope.

Figure 22:
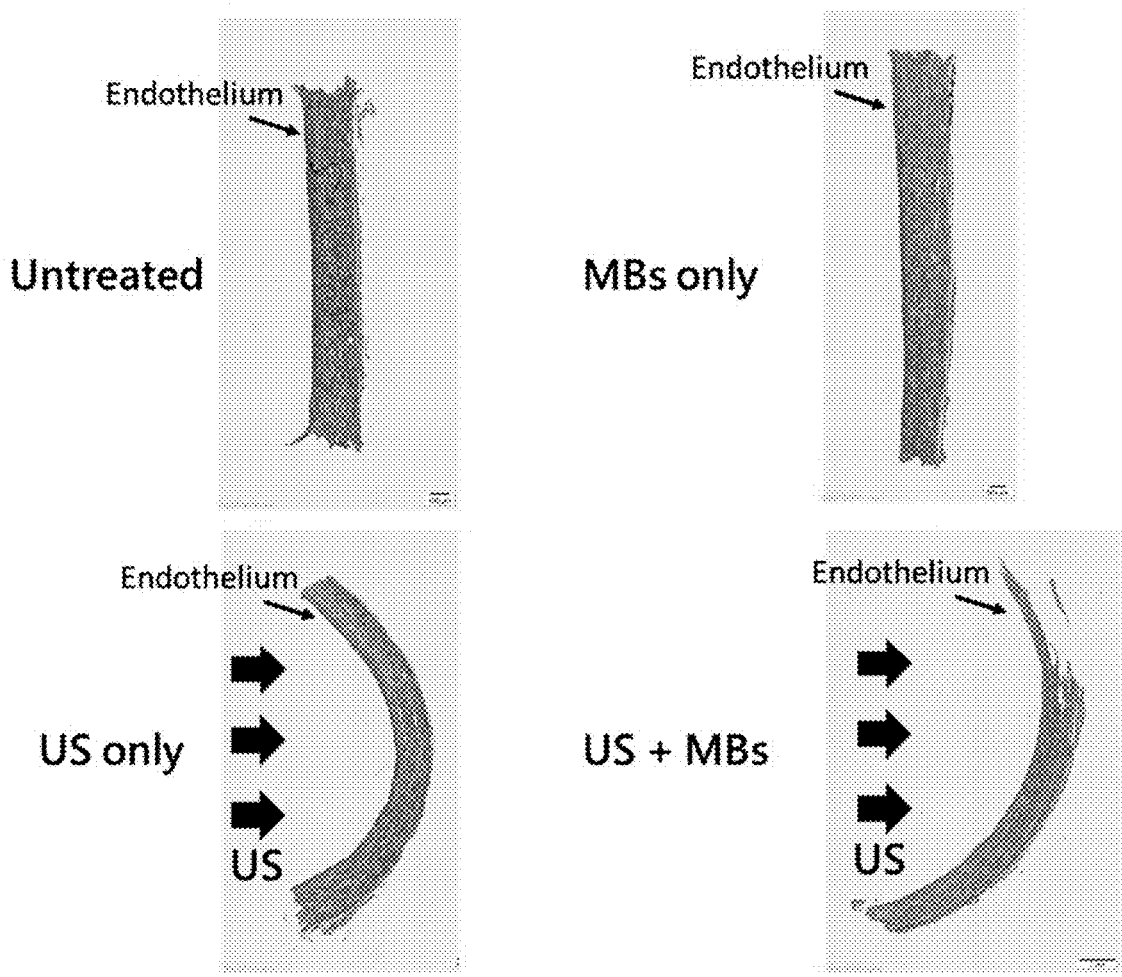
FIG. 22 shows results of FIG. 21.

Results:

Please refer to FIG. 22, results of the biological effects study. Damage on the endothelium is not found in all of the groups (Untreated, MBs only, US only, and US+MBs).

The above description is merely preferred embodiments of the present invention, and other equivalent structural and parameter changes of the present invention made in accordance with the disclosure and the scope of the invention are intended to be embraced in the scope of the present invention.

Therefore, the present invention has excellent advancement and practicability in similar products. Moreover, after searching for domestic and foreign technical documents concerning such products, it is true that no identical or similar structure or technology exists before the present application. Therefore, the present invention meets the patent requirements, and applied in accordance with the Patent Laws.

What is claimed is:

1. A balloon catheter system assisted by ultrasound and microbubbles, comprising:
   a controller;
   a sensor catheter, wherein the sensor catheter is configured to be provided into a blood vessel;
   a focused ultrasound probe, wherein the focused ultrasound probe and the sensor catheter are connected to the controller; and
   a balloon catheter,
   wherein the sensor catheter is removed from the blood vessel and the balloon catheter is configured to be inserted into the blood vessel;
   wherein microbubbles are infused into the balloon catheter and the focused ultrasound probe is controlled to start working to destroy a calcification point of a hardened portion of the blood vessel;
   wherein the balloon catheter at the hardened portion of the blood vessel is smoothly inflated; and
   wherein a solution composition of the microbubbles comprising three materials of:
   1,2-dipalmitoyl-sn-glycero-3-phosphocholine (DPPC);
   1,2-distearoyl-sn-glycero-3-phosphoethanolamine-N-[methoxy (polyethyleneglycol)-5000] (DSPE-PEG 5000]; and
   1,2-distearoyl-sn-glycero-3-phospho-(1'-rac-glycerol) (DSPG),
   wherein a weight ratio of the three materials is 2.5:1:1, and the three materials are dissolved in a combination of one or more of dichloromethane, chloroform, acetonitrile, methanol, or ethyl acetate, and followed by heating up and vortex mixing;
   wherein firstly 9800 cycles of lower-amplitude ultrasound is applied to create radiation force, and to push the microbubbles to the internal surface of the balloon catheter; then 200 cycles of higher-amplitude ultrasound is applied to create destruction force, whereby the microbubbles are destroyed due to the amplitude change.

2. A balloon catheter system assisted by ultrasound and microbubbles, comprising:
   a controller;
   a balloon catheter, wherein the balloon catheter is configured to be provided into a blood vessel; and
   at least one ultrasound transducer, wherein the ultrasound transducer is located within the balloon catheter, and the ultrasound transducer is connected to the controller;
   wherein microbubbles are infused into the balloon catheter and the ultrasound transducer is controlled to start working to destroy the microbubbles and generate shock waves;
   wherein the balloon catheter at a hardened portion of the blood vessel is smoothly inflated; and
   wherein a solution composition of the microbubbles comprising three materials of:
   1,2-dipalmitoyl-sn-glycero-3-phosphocholine (DPPC);
   1,2-distearoyl-sn-glycero-3-phosphoethanolamine-N-[methoxy (polyethyleneglycol)-5000] (DSPE-PEG 5000); and
   1,2-distearoyl-sn-glycero-3-phospho-(1'-rac-glycerol) (DSPG),
   wherein a weight ratio of the three materials is 2.5:1:1, and the three materials are dissolved in a combination of one or more of dichloromethane, chloroform, acetonitrile, methanol, or ethyl acetate, and followed by heating up and vortex mixing;
   wherein firstly 9800 cycles of lower-amplitude ultrasound is applied to create radiation force, and to push the microbubbles to the internal surface of the balloon catheter; then 200 cycles of higher-amplitude ultrasound is applied to create destruction force, whereby the microbubbles are destroyed due to the amplitude change.

* * * * *